(12) United States Patent
Wieters et al.

(10) Patent No.: US 12,185,915 B2
(45) Date of Patent: Jan. 7, 2025

(54) ACTUATOR SYSTEM FOR AN OPTICAL SYSTEM OF AN ENDOSCOPE AND OPTICAL SYSTEM FOR AN ENDOSCOPE

(71) Applicant: OLYMPUS Winter & Ibe GmbH, Hamburg (DE)

(72) Inventors: Martin Wieters, Barsbuettel (DE); Uwe Schoeler, Hoisdorf (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 537 days.

(21) Appl. No.: 17/550,181

(22) Filed: Dec. 14, 2021

(65) Prior Publication Data
US 2022/0202282 A1 Jun. 30, 2022

(30) Foreign Application Priority Data
Dec. 30, 2020 (DE) ...................... 10 2020 135 127.5

(51) Int. Cl.
*A61B 1/00* (2006.01)
(52) U.S. Cl.
CPC ................................ *A61B 1/00163* (2013.01)
(58) Field of Classification Search
CPC . A61B 1/00163; A61B 1/00096; A61B 1/051; A61B 1/00183; A61B 1/00; A61B 1/05
See application file for complete search history.

(56) References Cited

U.S. PATENT DOCUMENTS

| 2003/0043289 | A1 | 3/2003 | Konno | |
| 2004/0017620 | A1* | 1/2004 | Kaneko | G02B 7/02 359/823 |
| 2004/0220453 | A1* | 11/2004 | Jones | A61B 1/00096 600/160 |
| 2009/0021818 | A1* | 1/2009 | Weir | A61B 5/0062 359/224.1 |
| 2009/0303619 | A1* | 12/2009 | Iwasaki | G02B 23/243 310/306 |
| 2014/0275778 | A1* | 9/2014 | Gunday | A61B 1/00135 600/109 |
| 2015/0351879 | A1 | 12/2015 | Boltanski | |
| 2019/0170999 | A1* | 6/2019 | Schlenker | G02B 7/023 |

FOREIGN PATENT DOCUMENTS

DE  10 2004 018 110 A1  11/2004
DE  10 2017 128 668 A1  6/2019

OTHER PUBLICATIONS

Abstract only of US 2019/170999 A1.

* cited by examiner

*Primary Examiner* — Cara E Rakowski
*Assistant Examiner* — Jennifer A Jones
(74) *Attorney, Agent, or Firm* — Scully, Scott, Murphy & Presser, P.C.

(57) ABSTRACT

An actuator system for use in an optical system of an endoscope. The actuator system including: at least one actuator; and a holder for receiving at least one optical element of the optical system, the holder is configured to be flat and extends in a holder plane. The holder including: an outer enclosure; a leaf spring; and an inner platform. Wherein the outer enclosure at least partially surrounds the leaf spring and the leaf spring at least partially surrounds the inner platform, the outer enclosure is elastically coupled to the inner platform via the leaf spring, the inner platform is configured to receive the optical element, and the at least one actuator interacts with the inner platform.

21 Claims, 4 Drawing Sheets

ACTUATOR SYSTEM FOR AN OPTICAL SYSTEM OF AN ENDOSCOPE AND OPTICAL SYSTEM FOR AN ENDOSCOPE

CROSS-REFERENCE TO RELATED APPLICATION

The present application is based upon and claims the benefit of priority from DE 10 2020 135 127.5 filed on Dec. 30, 2020, the entire contents of which is incorporated herein by reference.

BACKGROUND

Field

The present disclosure relates generally to endoscopes and more particularly to an actuator system for an optical system of an endoscope and to an optical system for an endoscope.

Prior Art

In medical endoscopy, in addition to endoscopes with fixed optical systems, systems that enable switching between two working ranges, for example a near range and a is far range, are also known. This is typically achieved by a translation or tilting of an optical element by means of an actuator system.

In endoscopy, electromagnetic actuators, for example, are used as actuator systems, in which actuators include a traveler arranged in a tube of an endoscope which is moved axially by a magnetic field.

In many cases, the mobile element in actuator systems is guided in a fit. For this purpose, the fit must have mechanical play. Especially if tilting the mobile element is necessary in addition to a linear movement, this mechanical play must be relatively large, which results, however, in it being guided imprecisely. This has a disadvantageous effect on the image quality of the optical system of the endoscope.

SUMMARY

An object is to provide an actuator system for an optical system of an endoscope as well as an optical system for an endoscope, in which an optical element can be moved relatively within an optical system, precisely and with as little play as possible.

Such object can be solved by an actuator system for an optical system of an endoscope, comprising at least one actuator and a holder for receiving at least one optical element of the optical system, wherein the holder is configured to be flat and extends in a holder plane, wherein the holder has an outer enclosure, a leaf spring element, and an inner platform, wherein the outer enclosure at least partially surrounds the leaf spring element and the leaf spring element at least partially surrounds the inner platform, wherein the outer enclosure is elastically coupled to the inner platform by the leaf spring element, wherein the inner platform is configured to receive the optical element, and wherein the at least one actuator interacts with the inner platform.

In the context of the present description, the term "connect" refers to a direct connection between two components. The term "couple," on the other hand, refers to either a direct or an indirect connection between two components. An indirect connection between two components is thus a connection via additional components that are connected to each other.

The inner platform can be deflected and/or pivoted relative to the outer enclosure by at least one actuator in that the outer enclosure is coupled elastically to the inner platform via the leaf spring element. In other words, both a linear deflection and a tilting of the inner platform and thus of the optical element can be realized by the holder. By mounting the inner platform via the leaf spring element, an exceedingly precise guiding of the optical element can advantageously be achieved.

The actuator can interact with the inner platform such that it acts on the inner platform in order to deflect and/or tilt it. The at least one actuator can be configured to exert a displacement force on the inner platform. The holder can be configured to exert a resetting force on the inner platform, which is opposite to the displacement force. The at least one actuator can hold the inner platform under pretension. As a result, the deflection can be largely play-free. The at least one actuator can act on the inner platform along a linear operating direction that is perpendicular to the holder plane.

The outer enclosure can surround the leaf spring element, viewed in the holder plane, at least in portions in a radially peripheral manner. The outer enclosure can completely surround the leaf spring element. The leaf spring element can surround the inner platform, also viewed in the holder plane, at least in portions and in a radially peripheral manner. The leaf spring element can completely surround the inner platform.

According to one exemplary embodiment, in which the outer enclosure only partially surrounds the leaf spring element, existing cut-outs can be provided between the outer enclosure and the leaf spring element, which cut-outs can extend between the outer enclosure and the leaf spring element in a bar-shaped manner on opposite sides. According to such an exemplary embodiment, the outer enclosure can comprise a first part and an opposite second part. According to another exemplary embodiment, in which the leaf spring element only partially surrounds the inner platform, additional cut-outs can be provided between the leaf spring element and the inner platform, which cut-outs can also extend between the leaf spring element and the inner platform in a bar-shaped manner on opposite sides. These additional cut-outs can be arranged rotated, for example, by 90° in relation to the cut-outs. According to such an exemplary embodiment, the leaf spring element can comprise a first leaf spring part and an opposite second leaf spring part.

The outer enclosure, the leaf spring element, and the inner platform can be arranged concentrically to each other in the holder plane. Concentric means that the geometric center point of the outer enclosure, the leaf spring element, and the inner platform coincide. The outer enclosure can be configured to be fixed to the optical system. In the installed state of the actuator system, the outer enclosure can be fixed without play on a static part of the optical system.

According to one embodiment, the outer enclosure can have an annular shape. Such a shape can be advantageous if the holder is to be used, for example, in a cylindrical component. However, the outer enclosure can have other shapes, for example, elliptical, or rectangular.

According to an exemplary embodiment, the inner platform can have the shape of a rectangle. The leaf spring element can have a rectangular shape with rounded corners. According to other embodiments, however, leaf spring elements and inner platforms can have other shapes, for example, elliptical or circular.

The optical element can be, for example, a lens, a prism, a mask, or an image sensor. The optical element is not a component of the actuator system; the inner platform is only configured for receiving the optical element.

The outer enclosure can be connected to the leaf spring element exclusively by at least one first solid state hinge and the leaf spring element can be connected to the inner platform exclusively by at least one second solid state hinge.

With the solid state hinges, a completely play-free mounting of the inner platform can be achieved. In this way, the occurrence of reverse play or a slip-stick effect can be advantageously prevented. The solid state hinges can be configured as planar elements extending in the radial plane of the holder.

The at least one first solid state hinge and the at least one second solid state hinge can be arranged offset from each other in the holder plane, wherein the at least one first solid state hinge can be arranged offset from the at least one second solid state hinge by 90° along a holder circumferential direction lying in the holder plane.

The offset arrangement of the solid state hinges in the holder plane can advantageously increase the length of a leaf spring structure of the holder. The leaf spring structure can comprise in this case the leaf spring element and the solid state hinges and represents the part of the holder that couples the outer enclosure to the inner platform. The holder circumferential direction can be a direction in the holder plane running along the perimeter of the holder.

The holder can have two first solid state hinges and two second solid state hinges, wherein the first solid state hinges can be arranged on opposite sides of the leaf spring element and/or the second solid state hinges can be arranged on opposite sides of the leaf spring element.

By providing two first solid state hinges and two second solid state hinges in each case, the stability of the holder can be increased and a high reset force can be achieved.

The holder can be a single-piece component.

In other words, the outer enclosure, the leaf spring element, the inner platform, and the solid state hinges can be formed from a single blank. With the design as a single-piece component, the holder can be completely play-free with regard to a deflection by the at least one actuator.

A linear operating direction of the at least one actuator can project perpendicularly to the holder plane.

The linear operating direction can be a direction in which the at least one actuator exerts a displacement force on the inner platform. The linear operating direction can be parallel to an optical axis of the optical system. In addition, at least one tilt axis of the at least one actuator can lie in the holder plane.

The holder can be made from a cold-rolled stainless steel sheet, an amorphous metal, or from a nickel-titanium alloy, such as nitinol. It is also provided that the holder can be produced from multiple of these materials, wherein different functional units or portions, for example the outer enclosure, the leaf spring element, and the inner platform, can be produced from different materials. The use of nitinol can be advantageously used because such material has a pseudoelasticity or superelasticity.

Cold-rolled stainless steel sheets have a high modulus of elasticity. Amorphous metals have a very high modulus of elasticity due to their non-crystalline structure. Due to the high moduli of elasticity, the holders produced from these materials can have a strong reset force. Strong reset forces can be advantageous for the holder in order to realize the displacement paths of approx. 400 μm that are typical in actuator systems of endoscopes. However, considerably longer and shorter displacement paths can also be realized by the actuator system. Work hardening of stainless steel can increase the elastic range of the steel. A high elastic range of the material of the holder can be advantageous, since all deformations of the holder must be completely within the elastic range of the material in order to avoid material fatigue of the material.

The holder can have a material thickness of 50 μm to 150 μm, such as, about 100 μm. This material thickness can prevent the stresses in the holder from being too high when the material is deformed. At the same time, the necessary stability of the holder can be provided.

The leaf spring element can be mirror-symmetrical, wherein a first mirror plane of the leaf spring element can run through a center of the holder and is orthogonal to the holder plane, wherein a second mirror plane of the leaf spring element can run through the center of the holder and is orthogonal to the holder plane and to the first mirror plane.

The symmetrical structure can facilitate a linear translation of the inner platform. The entire holder can be mirror-symmetrical.

The at least one actuator can be fastened to the inner platform or to a component fixed to the inner platform.

The component fixed to the inner platform can be fastened to the inner platform by a fastener directly or indirectly. The actuator can act on the inner platform in that the displacement force of the actuator acts on the inner platform via the fastener.

The at least one actuator can be configured as at least one wire, such as, three or four wires, made of a shape-memory alloy, wherein the at least one wire can be coupled to a rear side of the inner platform.

A wire made of a shape-memory alloy (SMA) can advantageously take up only a small amount of space and has a low complexity, but achieves large forces and long adjustment paths. By providing three SMA wires, a deflection along the linear operating direction and a tilting about two tilt axes can be enabled. Four wires can be advantageous in the case of a rectangular inner platform when each corner of the inner platform is coupled with one wire. When four wires are used, a control system of the wires can be configured to compensate for the theoretical redundancy, resulting from the four wires, of the movement.

An insulator component can be fixed to the rear side of the inner platform, wherein the at least one wire can be fastened to the insulator component, wherein the insulator component can be formed at least partially from a synthetic material, wherein the insulator component can be soldered or screwed to the rear side of the inner platform.

Since SMA wires can develop their actuator effect when an electric current is conducted through them, it can be advantageous if the at least one wire is insulated from the holder by the insulator component. The insulator component can comprise of one or more components. Making the insulator component out of synthetic material can advantageously achieve the desired insulation. In order to join an insulator component made of synthetic material with the holder, such as, a 3D MID synthetic material can be used for the insulator. In this case, a metal layer can be applied to the synthetic material by a laser and electroplating and can then be soldered to the holder. According to an alternative embodiment, a metal component provided with a thread can be soldered, adhered, or welded to the holder and the insulator component can be fastened by the thread or a crimp connection.

Both ends of the at least one wire can be fixed to a holding device, which can be arranged proximally to the inner platform, wherein the at least one wire can be redirected at the insulator component.

The at least one wire does not have to be fixed to the holder or the insulator component, but only fastened there such that it is redirected by approx. 180°. Advantageously, the force of the at least one wire acting as an actuator can be doubled in this way. In addition, no electrical contact of the at least one wire with the holder or the insulator component is necessary. The wire can be hooked into a matching contour in the holder or the insulator component or drawn through the contour. The term "proximal" refers in the present case to the alignment of the holder. In other words, the holding device is arranged to the rear of the inner platform. The at least one wire can be electrically contacted by the holding device.

According to one embodiment, the holder can be fixed to a first end of a housing, such as a hollow cylindrical housing, wherein the at least one wire can be guided through the housing and fixed to a second end of the housing, such as an end disk of the housing.

With the housing, a stable mounting of the at least one wire can be advantageously achieved. A hollow cylindrical shape of the housing can be advantageous in order to insert the housing into a cylindrical component in the interior of the endoscope shaft. The end disk can close in the second end of the housing. The at least one wire can be electrically contacted by means of the end disk.

The holding device, on which both ends of the at least one wire are fixed, can be arranged on the second end of the housing, wherein the holding device can be the end disk of the housing.

In this way, the at least one wire can be electrically contacted on both ends by the holding device, such as, the end disk.

A central region of the inner platform can have a cut-out.

A cut-out in the central region of the inner platform can be advantageous if, for example, a lens, a prism, or a mask is provided as an optical element. The cut-out can be large enough not to block the beam path of light bundles running through the optical element.

According to one embodiment, the holder itself can be configured as a mask for the optical element. In this case, the holder can be blackened or made from a black material. According to an alternative embodiment, the inner platform can be a complete surface and has no cut-outs. This is practical, for example, if the inner platform is configured for receiving an image sensor.

Such object can also be solved by an optical system for an endoscope, comprising an actuator system according to one of the embodiments described above, and an optical element, wherein the outer enclosure of the holder is fixed to a static part of the optical system and the optical element is fixed to the inner platform of the holder.

The same or similar advantages as already explained above with respect to the actuator system also apply to the optical system. In the present case, the static part of the optical system can be a component of the optical system that does not move when the actuator system is deflected. The outer enclosure can be fixed without play to the static part of the optical system.

The optical element can be soldered or adhered to the holder. The optical element can have a flat face perpendicular to the linear operating direction of the actuator. This can facilitate the fastening of the optical element to the holder.

The inner platform can have an indentation, in which the optical element can be arranged so that an optically active face of the optical element can lie in the holder plane.

The optically active face can be, for example, an active face of an image sensor or a primary plane of a lens. By the indentation, the active face can be aligned parallel to the holder plane. This can advantageously reduce or completely avoid a parallax error, which would otherwise occur when tilting the optical element.

The indentation can be produced by deep drawing. Alternatively, the indentation can project completely through the inner platform, in which a separate component can be received which holds the optical element. The separate component can create a guide, for example with a hollow cylindrical shape, that holds the optical element or a frame of the optical element precisely and securely.

BRIEF DESCRIPTION OF THE DRAWINGS

Further features will become apparent from the description of the embodiments together with the claims and the attached drawings. Embodiments can fulfill individual features or a combination of several features.

The embodiments are described below, without restricting the general idea of the invention, based on exemplary embodiments in reference to the drawings, whereby we expressly refer to the drawings with regard to details that are not explained in greater detail in the text. In the figures.

In the drawings, the same or similar elements and/or parts are provided with the same reference numbers; a reintroduction will therefore be omitted.

DETAILED DESCRIPTION

Figure 1:
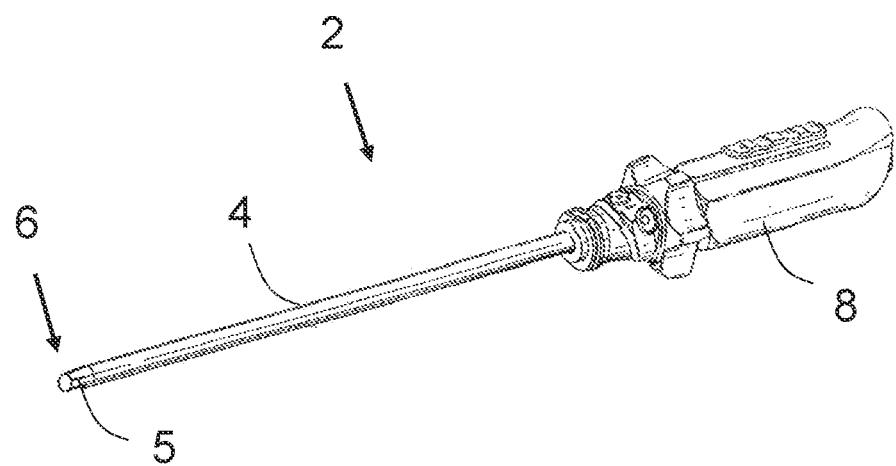
FIG. 1 illustrates a schematically simplified illustration of an endoscope.

FIG. 1 shows, schematically simplified, an endoscope 2 in a perspective illustration. The endoscope 2 comprises a handle 8 and a shaft 4, configured to be inserted into the interior of a patient's body. In the interior of the shaft 4, an optical system 5 of the endoscope 2 is arranged, for observing a space lying in front of the distal end 6 of the endoscope 2. Such observation occurs through a series of optical elements of the optical system 5, such as lenses, prisms, and image sensors, which capture image information and transmit it in a proximal direction.

For some medical procedures using the endoscope 2, it is advantageous when the user can switch the endoscope 2 between two different working ranges, for example a near range and a far range, so that regions of the interior of the body lying directly in front of the distal end 6 as well as regions lying farther away can be observed with high image quality. To enable switching between two working ranges, some endoscopes 2 comprise an actuator system, for moving one or more of the optical elements of the optical system 5.

Figure 2:
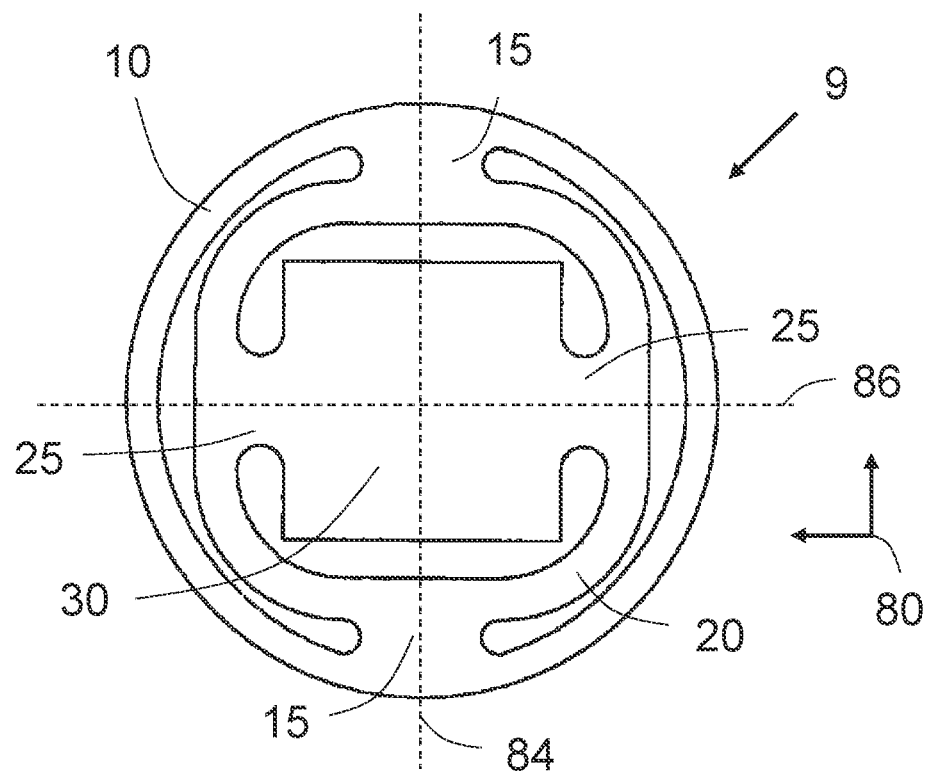
FIG. 2 illustrates a schematically simplified illustration of a holder for an optical element.

FIG. 2 shows, schematically simplified, an exemplary embodiment of a holder 9 of an actuator system. The holder 9 comprises an outer enclosure 10, a leaf spring element 20, and an inner platform 30. The inner platform 30 is configured to receive the optical element to be moved. The outer enclosure 10 is fixed to a static part of the optical system 5.

In the embodiment shown, the outer enclosure 10 is annular and surrounds the leaf spring element 20 completely in a holder plane 80. In FIG. 2, the holder plane 80 lies in the plane of the image, as indicated by the two arrows arranged orthogonally to each other. The outer enclosure 10 is connected to the leaf spring element 20 by two first solid state hinges 15, which are arranged on opposite sides of the leaf spring element 20. The leaf spring element 20 is in turn connected to the inner platform 30 by means of two second solid state hinges 25. The two second solid state hinges 25 are also arranged on opposite sides of the leaf spring element 20 and offset by 90° to the first solid state hinges 15 in the holder plane 80. As a result, a mirror symmetry of the leaf spring element 20 and the entire holder 9 results, with a first mirror plane 84 and a second mirror plane 86, each shown by dashed lines, which are orthogonal to each other and to the holder plane 80.

The inner platform 30 interacts with at least one actuator, which is not shown in FIG. 2. This at least one actuator exerts a displacement force on the inner platform 30 in order to change the position and alignment of the inner platform 30, or respectively of the optical element, in relation to the outer enclosure 10 or respectively the optical system 5. A reset force opposite to the displacement force is exerted by the leaf spring element 20 and the solid state hinges 15, 25, which together form a leaf spring structure. Due to this reset force, the inner platform 30 and thus also the optical element is brought back to its starting position once the displacement force is no longer exerted on the inner platform 30.

The holder 9 shown is completely free of play. For this purpose, the holder 9 can be produced from a single component. A cold-rolled stainless steel sheet or amorphous metals can be suitable materials for the holder 9 since they have a high modulus of elasticity and develop high reset forces and at the same time have a large elastic range.

Figure 3:
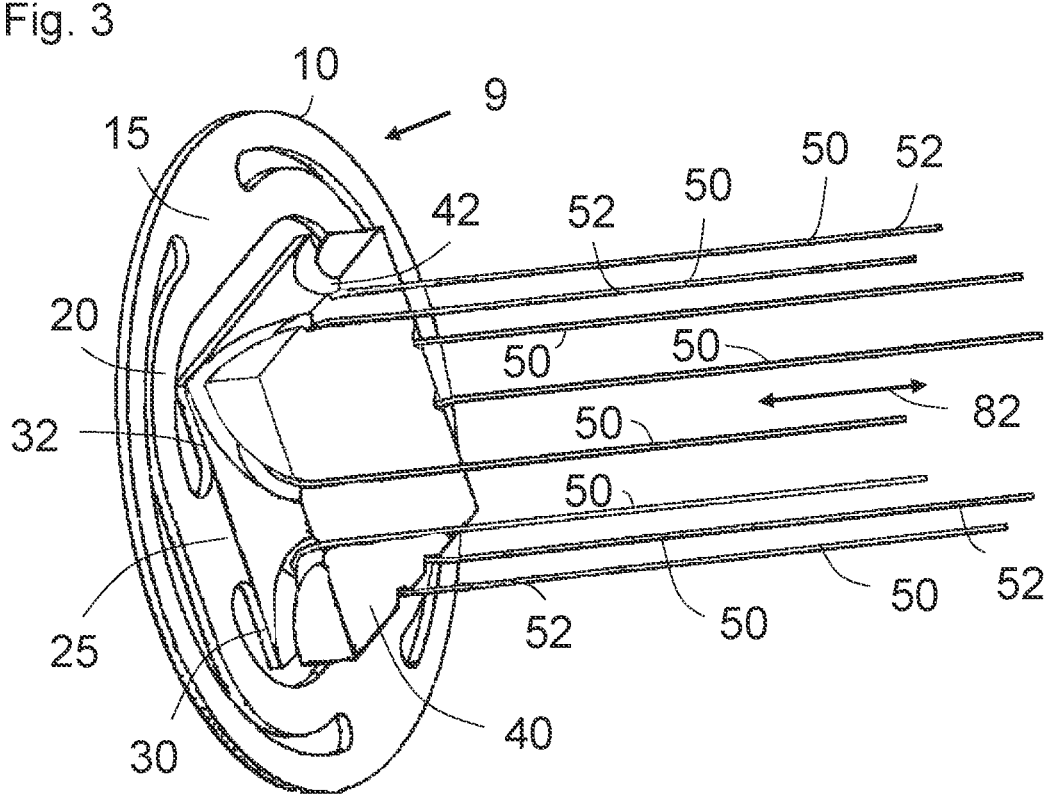
FIG. 3 illustrates a schematically simplified perspective illustration of a holder for an optical element having an insulator component and four SMA wires.

FIG. 3 shows, schematically simplified, an exemplary embodiment of a coupling, which connects the holder 9 to the at least one actuator 52. In this embodiment, an insulator component 40 is fixed to a rear side 32 of the inner platform 30. The insulator component 40 has a series of indentations or contours 42, in which wires 50 made of a shape-memory alloy (SMA) are guided. The SMA wires 50 are the actuators 52 of the actuator system. They are not firmly fixed to the insulator component 40 but are merely redirected on it by being guided through the contours 42. FIG. 3 shows a total of four wires 50 redirected in this manner, each with two wire ends. To deflect the inner platform 30, an electric current is conducted through the wires 50. This leads to a heating of the wires 50, which then contract, causing a displacement force to be exerted on the insulator component 40 and thus on the inner platform 30. By correspondingly activating the wires 50 acting as actuators 52, the inner platform 30 can be both deflected perpendicularly to the holder plane 80 in a linear operating direction 82 and tilted in relation to the holder plane 80. The insulator component 40 is produced from an insulating material in order to electrically shield the wires 50 from each other and from the holder 9.

Figure 4:
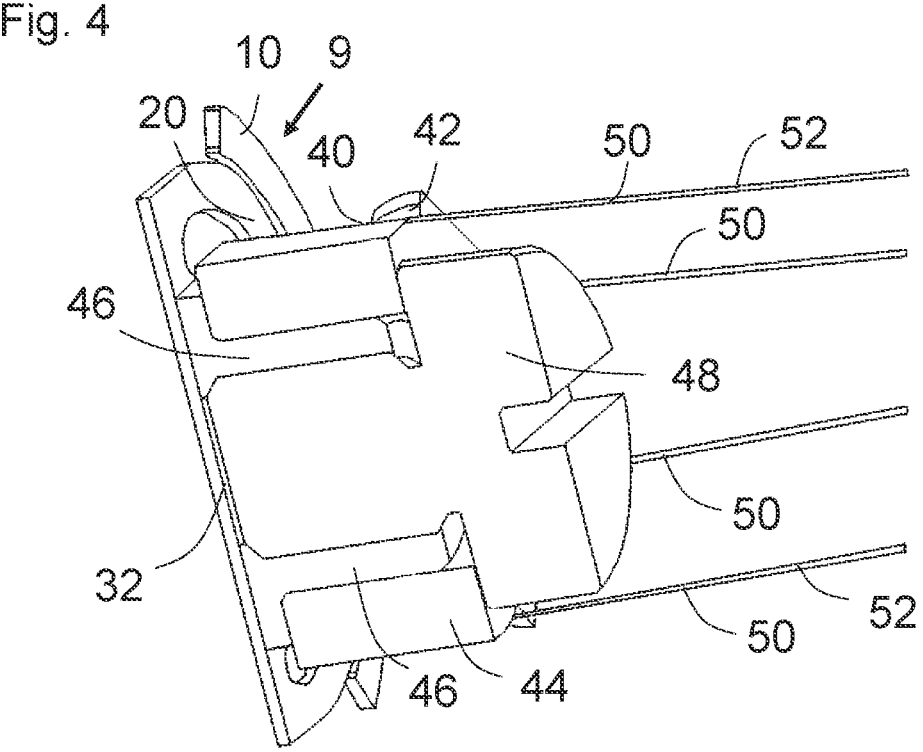
FIG. 4 illustrates a schematically simplified perspective illustration of a fastener for an insulator component on a holder by means of a screw.

FIG. 4 shows, schematically simplified, another embodiment of an insulator component 40 in a cross-sectional view. The insulator component 40 shown in FIG. 4 comprises an insulated wire mount 44, an adapter 46 with a thread, and a screw 48. The adapter 46 is produced, for example, from a metal and soldered to the rear side 32 of the inner platform 30. The insulated wire mount 44, which is produced, for example, from a synthetic material, is placed onto the adapter 46 and then fixed by means of the screw 48.

Figure 5:
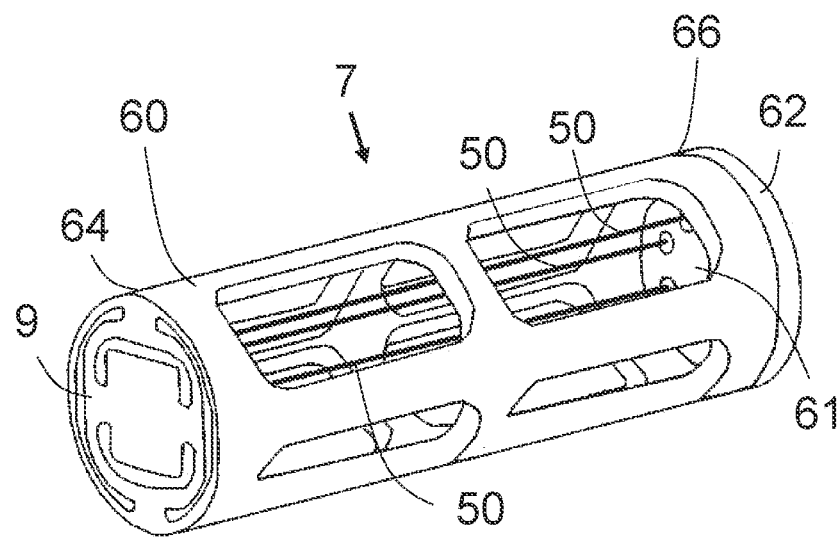
FIG. 5 illustrates a schematically simplified illustration of a hollow cylindrical housing of an actuator system.

FIG. 5 shows, schematically simplified, an actuator system 7 that comprises the holder 9 from FIG. 2. The holder 9 is fixed to a first end 64 of a hollow cylindrical housing 60. The SMA wires 50 acting as actuators 52, which are fixed, for example, by means of a mount according to FIG. 3 or FIG. 4, to the rear side 9 of the holder, are guided through the interior of the housing 60 and fixed with both ends to a holding device 61 that is arranged on the second end 66 of the housing. In the embodiment shown, the holding device 61 is an end disk 62 of the housing 60.

Figure 6:
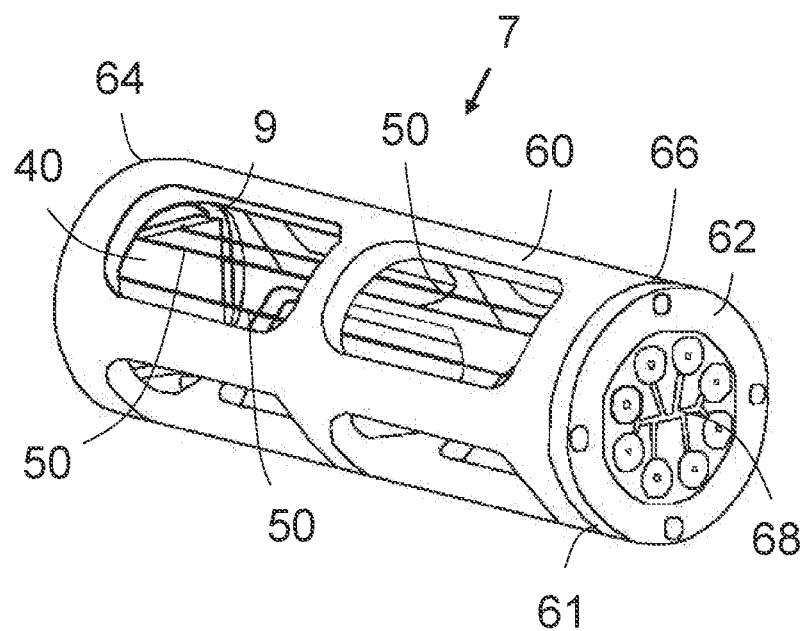
FIG. 6 illustrates a schematically simplified perspective illustration of a hollow cylindrical housing of an actuator system on the rear side of the housing.

In FIG. 6, the housing 60 from FIG. 5 is shown, schematically simplified, in a perspective view, in which the end disk 62 can easily be seen. The end disk 62 comprises an electrical contact 68, by means of which the wires 50 are supplied with electric current.

Figure 7:
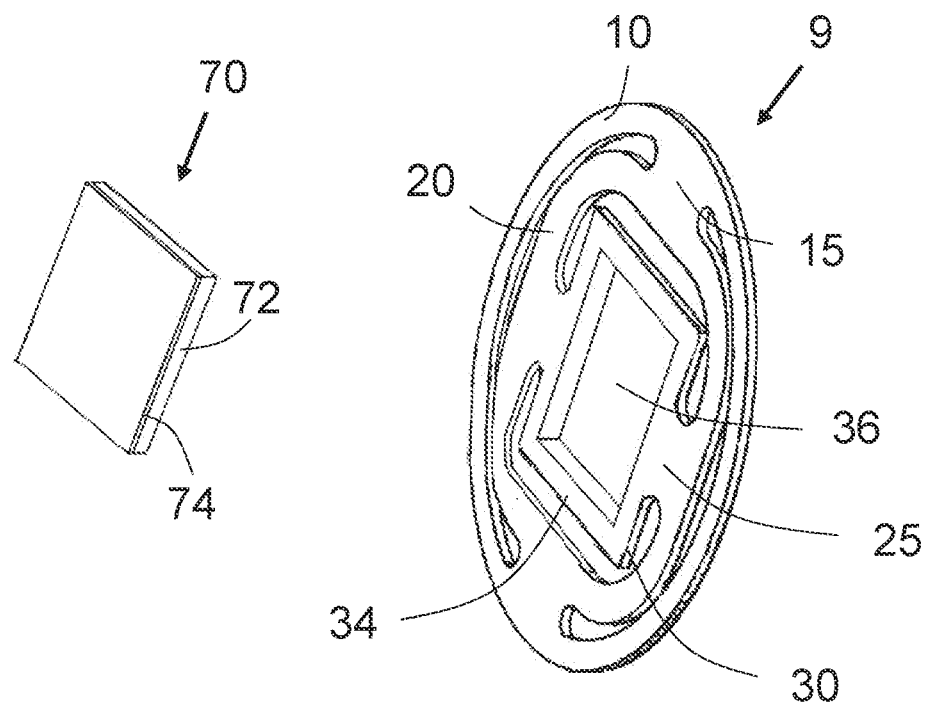
FIG. 7 illustrates a schematically simplified perspective illustration of an image sensor as well as a holder for the image sensor with an indentation for receiving the image sensor.

FIG. 7 shows, schematically simplified, an embodiment of a holder 9 that comprises an inner platform 30 with an indentation 36 on its front side 34. The indentation 36 is produced, for example, by deep drawing. An optical element 70, for example the image sensor 72 shown in FIG. 7, is inserted into the indentation 36. This enables that an active face 74 of the optical element 70 lies in the holder plane 80. In this way, a parallax error that could occur when tilting the optical element 70 is reduced or completely avoided.

Figure 8:
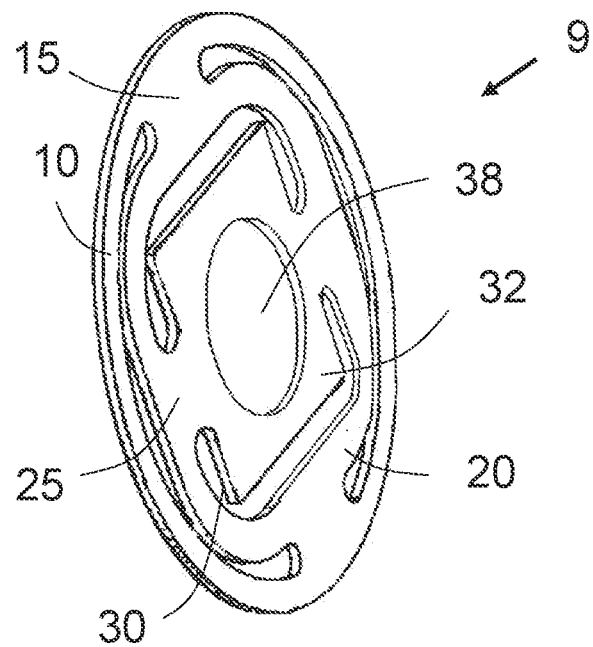
FIG. 8 illustrates a schematically simplified perspective illustration of a holder with a cut-out in a central region of the inner platform.

FIG. 8 shows another exemplary embodiment of a holder 9 that has a cutout 38 in a central region of the inner platform 30. Such a cut-out 38 is practical when, for example, a lens is fixed to the inner platform 30, in order not to impair the beam path of light bundles running through the lens. Another component (not shown) that holds the optical element 70 can also be inserted into the cut-out 38. In this way, a secure hold of the optical element 70 is achieved. According to another embodiment, it is provided that the holder 9 is blackened or produced from a black material. In this case, the inner platform 30 with the cut-out 38 forms a deflectable mask for the optical system 5.

While there has been shown and described what is considered to be embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

LIST OF REFERENCE NUMBERS

2 Endoscope
4 Shaft
5 Optical system
6 Distal end

7 Actuator system
8 Handle
9 Holder
10 Outer enclosure
15 First solid state hinge
20 Leaf spring element
25 Second solid state hinge
30 Inner platform
32 Rear side
34 Front side
36 Indentation
38 Cut-out
40 Insulator component
42 Contour
44 Insulated wire mount
46 Adapter
48 Screw
50 Wire
52 Actuator
60 Housing
61 Holding device
62 End disk
64 First end
66 Second end
68 Electrical contact
70 Optical element
72 Image sensor
74 Active face
80 Holder plane
82 Linear operating direction
84 First mirror plane

What is claimed is:

1. An actuator system for use in an optical system of an endoscope, the actuator system comprising:
at least one actuator; and
a holder for receiving at least one optical element of the optical system, the holder is configured to be flat and extends in a holder plane, the holder comprising:
an outer enclosure;
a leaf spring; and
an inner platform;
wherein the outer enclosure at least partially surrounds the leaf spring and the leaf spring at least partially surrounds the inner platform,
the outer enclosure is elastically coupled to the inner platform via the leaf spring,
the inner platform is configured to receive the optical element,
the at least one actuator interacts with the inner platform; and
the holder is formed from one of a cold-rolled stainless steel sheet, an amorphous metal, or a nickel-titanium alloy.

2. The actuator system according to claim 1, wherein the outer enclosure is connected to the leaf spring by at least one first solid state hinge and the leaf spring is connected to the inner platform by at least one second solid state hinge.

3. The actuator system according to claim 2, wherein the at least one first solid state hinge and the at least one second solid state hinge are arranged offset from each other in the holder plane.

4. The actuator system according to claim 3, wherein the at least one first solid state hinge is arranged offset from the at least one second solid state hinge by 90° along a holder circumferential direction lying in the holder plane.

5. The actuator system according to claim 2, wherein the at least one first solid state hinge comprises two first solid state hinges and the at least one second solid state hinge comprises two second solid state hinges.

6. The actuator system according to claim 5, wherein at least one of the two first solid state hinges are arranged on opposite sides of the leaf spring and the two second solid state hinges are arranged on opposite sides of the leaf spring.

7. The actuator system according to claim 1, wherein the holder is a single-piece component.

8. The actuator system according to claim 1, wherein a linear operating direction of the at least one actuator projects perpendicularly to the holder plane.

9. The actuator system according to claim 1, wherein the leaf spring is mirror-symmetrical about a first mirror plane extending through a center of the holder, the first mirror plane being orthogonal to the holder plane.

10. The actuator system according to claim 9, wherein the leaf spring is further mirror-symmetrical about a second mirror plane extending through the center of the holder, the second mirror plane being orthogonal to the holder plane and to the first mirror plane.

11. The actuator system according to claim 1, wherein the at least one actuator is fastened to the inner platform or to a component fixed to the inner platform.

12. The actuator system according to claim 1, wherein the at least one actuator is configured as at least one wire formed of a shape-memory alloy, wherein the at least one wire is coupled to a rear side of the inner platform.

13. The actuator system according to claim 12, wherein the at least one wire comprises two or more wires, each formed of the shape memory alloy and each coupled to the rear side of the inner platform.

14. The actuator system according to claim 12, further comprising an insulator component fixed to the rear side of the inner platform, wherein the at least one wire is fastened to the insulator component.

15. The actuator system according to claim 14, further comprising a holding device arranged proximally to the inner platform, wherein each of two ends of the at least one wire are fixed to the holding device, wherein each of the two ends are redirected to the holding device by the insulator component.

16. The actuator system according to claim 12, further comprising a cylindrical housing, wherein the holder is fixed to a first end of the cylindrical, housing, and the at least one wire is guided through the cylindrical housing and fixed to a second end of the cylindrical housing.

17. The actuator system according to claim 16, further comprising an end disk fixed to the second end of the housing, the at least one wire being fixed to the end disk.

18. The actuator system according to claim 1, wherein a central region of the inner platform has a cut-out.

19. An optical system for use in an endoscope, the optical system comprising:
an actuator system according to claim 1; and
the at least one optical element;
wherein the outer enclosure of the holder is fixed to a static part of the optical system and the optical element is fixed to the inner platform of the holder.

20. The optical system according to claim 19, wherein the inner platform has an indentation in which the optical element is arranged so that an optically active face of the optical element lies in the holder plane.

21. An actuator system for use in an optical system of an endoscope, the actuator system comprising:
at least one actuator; and a holder for receiving at least one optical element of the optical system, the holder is configured to be flat and extends in a holder plane, the holder comprising:
an outer enclosure;
a leaf spring; and
an inner platform;
wherein:
the outer enclosure at least partially surrounds the leaf spring and the leaf spring at least partially surrounds the inner platform,
the outer enclosure is elastically coupled to the inner platform via the leaf spring,
the inner platform is configured to receive the optical element,
the at least one actuator interacts with the inner platform; and
the at least one actuator is configured as at least one wire formed of a shape-memory alloy, wherein the at least one wire is coupled to a rear side of the inner platform; and
the actuator system further comprising:
an insulator component fixed to the rear side of the inner platform, wherein the at least one wire is fastened to the insulator component; and
a holding device arranged proximally to the inner platform, wherein each of two ends of the at least one wire are fixed to the holding device, wherein each of the two ends are redirected to the holding device by the insulator component.

\* \* \* \* \*